United States Patent [19]

Peery et al.

[11] Patent Number: 4,505,702

[45] Date of Patent: Mar. 19, 1985

[54] MANUALLY OPERABLE ROTARY SYRINGE

[75] Inventors: John R. Peery, Palo Alto; James B. Eckenhoff, Los Altos, both of Calif.

[73] Assignee: ALZA Corporation, Palo Alto, Calif.

[21] Appl. No.: 452,552

[22] Filed: Dec. 23, 1982

[51] Int. Cl.³ ............................................. A61M 5/00
[52] U.S. Cl. .................................. 604/209; 604/246; 222/386
[58] Field of Search ............... 604/187, 207, 209, 211, 604/246; 222/386, 390, 391

[56] References Cited

U.S. PATENT DOCUMENTS

| 2,375,430 | 5/1945 | Mason et al. | 222/386 |
|---|---|---|---|
| 2,656,953 | 10/1953 | Rich | 222/386 |
| 3,517,662 | 6/1970 | Brickson | 604/209 |
| 4,270,532 | 6/1981 | Franetski et al. | |
| 4,298,000 | 11/1981 | Thill et al. | |
| 4,300,554 | 11/1981 | Hessberg et al. | |
| 4,320,757 | 3/1982 | Whitney et al. | |
| 4,340,048 | 7/1982 | Eikenhoff | |

OTHER PUBLICATIONS

Per Pump Infuser, Instruction Manual, 24 pp.

Primary Examiner—Stephen C. Pellegrino
Attorney, Agent, or Firm—Steven F. Stone; Edward L. Mandell; Paul L. Sabatine

[57] ABSTRACT

A manually operated rotary syringe comprises a fixed base member and a relatively rotable cap member, one of which has an arcuate recess and the other of which carries a mating plug which is received in the arcuate recess in fluid tight relationship with the walls of the recess. Outlet means extend through the stationary base from one end of the arcuate recess such that on rotation of the cap the plug will be caused to traverse the recess towards the outlet to expel the contents of the recess through the outlet means in the base. Means are provided to permit rotation of the cap with respect to the base in only in the direction of operation.

7 Claims, 5 Drawing Figures

MANUALLY OPERABLE ROTARY SYRINGE

FIELD OF THE INVENTION

This invention relates to a manually operated dispenser capable of providing a multiplicity of individual fluid pulses of predetermined size and more particularly to a rotary syringe capable of providing a multiplicity of individual pulses or one continuous bolus of a biologically active material for introduction into the body of a patient.

BACKGROUND OF THE INVENTION

The typical syringe known to the prior art consists of a generally cylindrical hollow barrel having a close fitting piston adapted to seat within the body and, on activation, drive the contents of the syringe through an outlet at one end. The outlet is normally connected to a hypodermic or other type of needle or cannula to direct the contents into a patient or to another site of use. Such syringes are typically transparent and provided with indicia to provide, with reference to the piston, a visual measurement of the initial volume of the contents of the syringe and the volume that is displaced by partial or total introduction of the piston into the barrel. Such devices have been in use for many years and are normally quite adequate for their intended functions. Recent advances in chemotherapy, however, have developed a need for small compact syringes which can be worn on the body of a subject and operated repeatedly during their life cycle to discharge a series of fluid pulses. A typical application would be in the administration of insulin to diabetics. Various manual, mechanical, electrical and osmotic portable infusion devices are known to the art as represented by the U.S. Pat. Nos. 4,270,532, 4,298,000, 4,300,554, 4,320,757 and 4,340,048. U.S. Pat. No. 4,340,048 also discloses a manually operated pulse supplement to an osmotically produced tonic flow in which the pulse is initiated by relative rotation of a threaded member which drives a piston longitudinally into a drug reservoir.

We have found that rotational actuation of a syringe presents significant advantages over longitudinal actuation, particularly with respect to manually operated, body mounted pumps and according to this invention we have optimized construction of a rotary syringe to produce a positive, irreversible, precisely controlled rotary syringe having a minimum number of moving parts and an extremely compact size.

It is accordingly an object of this invention to provide a manually actuated rotary syringe.

It is another object of this invention to provide a rotary syringe which is irreversible in action.

It is another object of this invention to provide a rotary syringe adapted to administer a plurality of precisely determined pulse dosages.

It is another object of this invention to provide a rotary syringe in which the operational status of the device is visually observable.

These and other objects of the invention will be readily apparent from the following description with reference to the accompanying drawings; wherein.

DESCRIPTION OF THE INVENTION

Figure 1:
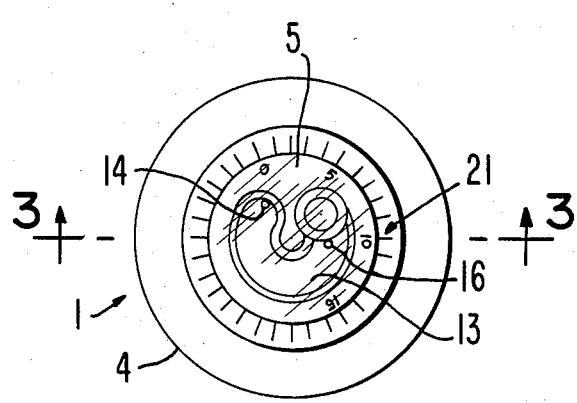
FIG. 1 is a plan view of an embodiment of this invention.
Figure 2:
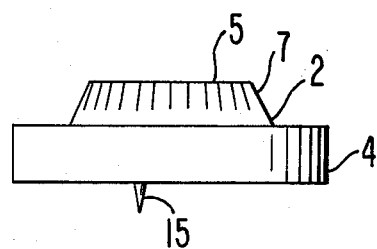
FIG. 2 is a side view of the embodiment of FIG. 1.
Figure 3:
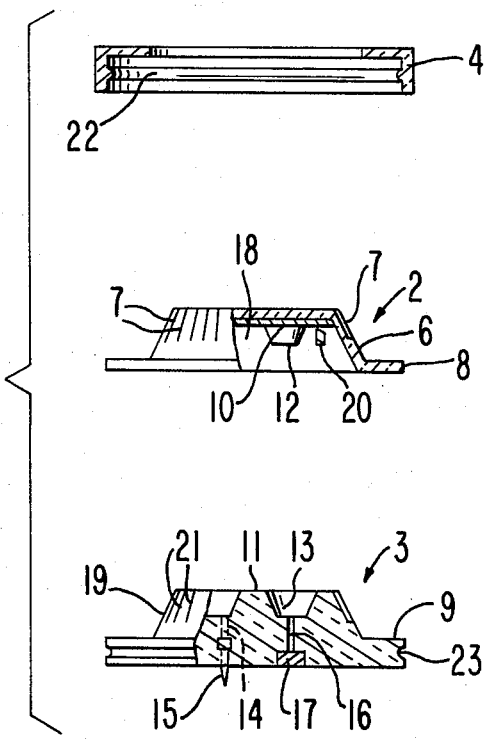
FIG. 3 is an exploded side view partially in section showing the internal construction of the embodiment of FIG. 1 and 2.

As shown in FIGS. 1-3 a rotary syringe 1 comprises a cap 2, a base member 3, which may also be formed from a transparent material, and a snap ring 4 adapted to maintain the cap 2 and base 3 in rotational interrelationship. Cap 2 and base 3 in FIGS. 1-3 are formed from transparent materials such that the interior structure of syringe 1 and its contents are visible through the transparent top 5 of cap 2. The side wall 6 of cap 2 preferably tapers outwardly from top 5 and is knurled at 7 to facilitate rotation of the cap 2 with respect to base 3. The bottom of cap 2 terminates in an annular extending flange 8, the surface of which is flat and adapted to rest on a similarly located annular flange 9 formed about the periphery of base 3. The inner surface of top 5 has mounted thereon a circular gasket 10 which is preferably substantially coextensive with the top surface 5 and of sufficient thickness to provide a fluid tight seal between the interior of cap 2 and the top surface 11 of base 3. A plug 12 depends from gasket 10 and may either be formed integrally therewith or otherwise firmly attached thereto. Plug 12 is configured to be in fluid sealing relationship to the side and base surfaces of reservoir 13 which is defined by an annular recess formed by machining or molding or otherwise in the top of base member 3. The ends of reservoir 13 are adapted to conform to the exterior of plug 12 in fluid sealing relationship and the side surfaces are defined by semicircular walls having a common center such that upon rotation of cap 2, plug 12 may traverse from the position shown in FIG. 1 to the opposite end of the reservoir over outlet port 14 as a piston in a fluid sealing manner to thereby displace through outlet port 14 formed in body 3 and through a needle or other fluid conduit 15, the fluid contents of the reservoir 13. An inlet port 16 is also provided at the opposite end of the reservoir 13 and spaced therefrom by at least the distance of the diameter of the base of plug 12 to permit the filling of reservoir 13 through resealable septum 17. Needle 15 is maintained in place in the outlet port 14 by screw threads or a frictional fit or any suitable means.

The interior side wall 18 of cap 2 and the exterior side wall 19 of base member 3, are parallel so that cap 2 may be nested on base 3 with side walls 18 and 19 in close fitting relationship. A plurality of preferably uniformly spaced pawls 20 are associated with internal side wall 18 and are adapted to engage a multiplicity of ratchet teeth 21 formed on the exterior side wall 19 to form a ratchet mechanism which permits rotation of the cap 2 with respect to the base 3 only in one direction. In the embodiment shown this is the clockwise direction such that piston 12 will rotate from the position shown in FIGS. 1 and 3 to the opposite end of reservoir 13 thereby forcing the fluid contents which are in reservoir 13 out through outlet port 1.4. To assemble the device, cap 2 would be placed on base 3 with flange 8 resting on flange 9 and snap ring 4 slipped over cap 2 and held in place by means of annular tongue 22 which is engaged in annular groove 23 around the periphery of the base member 3. Snap ring 23 is adapted to maintain the cap 2 on base 3 with sufficient pressure such that gasket 19 within the top of cap 2 forms a fluid tight seal between the top of base 3 to prevent fluid within reservoir 13 from escaping from the reservoir other than through outlet 14. A suitable medical lubricant such as Dow Corning 60 Medical Fluid may be applied to the abutting surfaces 8, 9 and the top 11 of base 3 to facilitate the rotational motion of the cap 2 and the base 3 without binding or the material for gasket 10 can be selected to have a suitable slip agent incorporated therein. The rotary syringe can be calibrated by appropriate selection of the size and spacing of the teeth 21 such that the rotation of the cap one notch will discharge a predetermined quantity of fluid. To facilitate use, cap 2 and base 3 can be provided with suitable marking indicia such as arrow 24 molded or printed on cap 2 and indicia 25 printed or molded on the perphery of the upper surface 11 of base 3 and visible through the transparent top 5 of cap 2 such that the user will have a visual indication of quantity of the material consumed and of the remaining amount in the injector.

In use, the material desired to be dispensed would be filled into reservoir 13 by introduction from a suitable needle inserted through septum 17 and charged into the reservoir until a steady stream of fluid is emitted through needle 15 to eliminate any air from the chamber. The needle 15 could then be inserted into the skin or the outlet 14 connected to any desired sites of use.

The rotary syringe of this invention may be mounted directly on the body with the needle 15 penetrating into the subcutaneous space as is known to the art. In this situation, the lower surface of the pump assembly could be provided with a body compatible adhesive or the pump assembly could be maintained in place by an adhesive overlay or any suitable strap, belt or elastic fastening means, for example. Rather than penetrating the body directly at the situ of use, the outlet 14 could be connected to a catheter or a cannula for delivery to a remote location, or the syringe can be used in conjunction with a pump assembly which provides a tonic flow rate which can be supplemented by needed pulses from the rotary syringe by placing outlet 14 in fluid communication with the fluid reservoir of such a pump such as is disclosed for example in co-pending co-assigned patent application of Eckenhoff, et. all for Body Mounted Pump Housing and Pump Assembly Employing the Same, filed Dec. 23, 1982, Ser. No. 452,523. In addition, as shown in FIGS. 4 and 5, the rotary syringe of this invention can also be formed integrally with another pump assembly whereby the tonic flow produced by the pump can be supplemented with needed manually instigated pulses.

Figure 4:
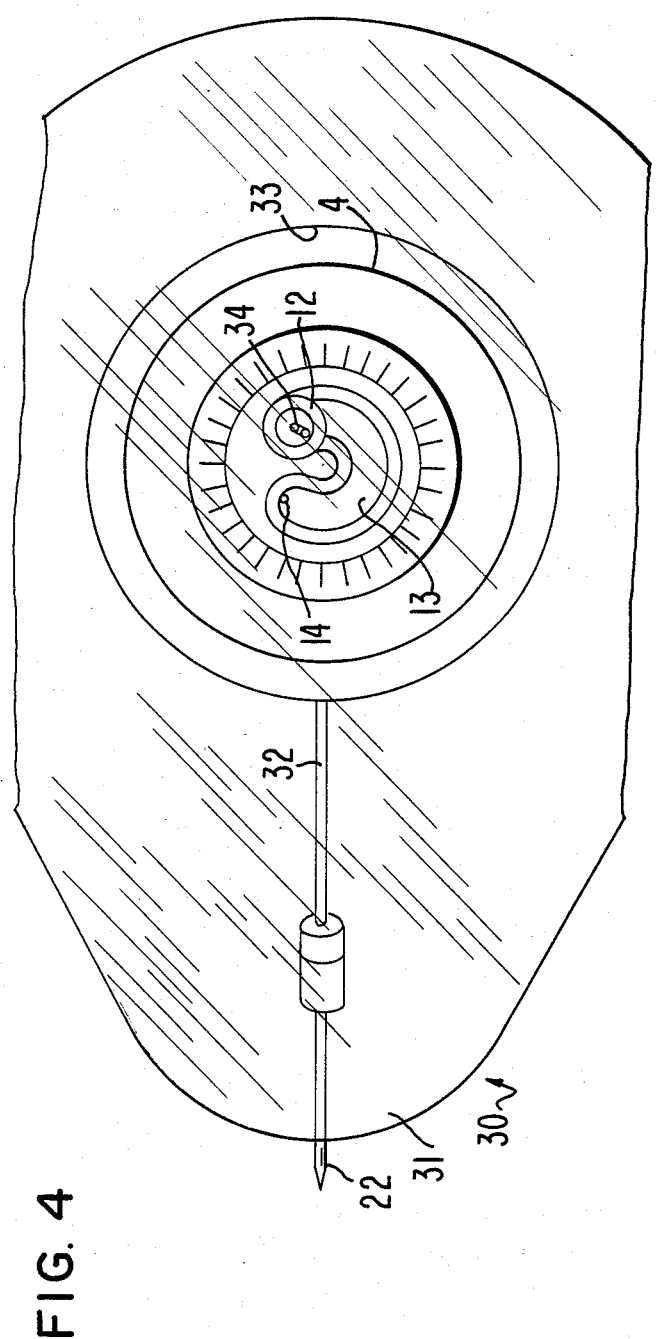
FIG. 4 is a top view of an embodiment of this invention formed integrally with a pump capable of producing a constant basal flow rate and FIG. 5 is a side view partly broken away of the embodiment of FIG. 4.
Figure 5:
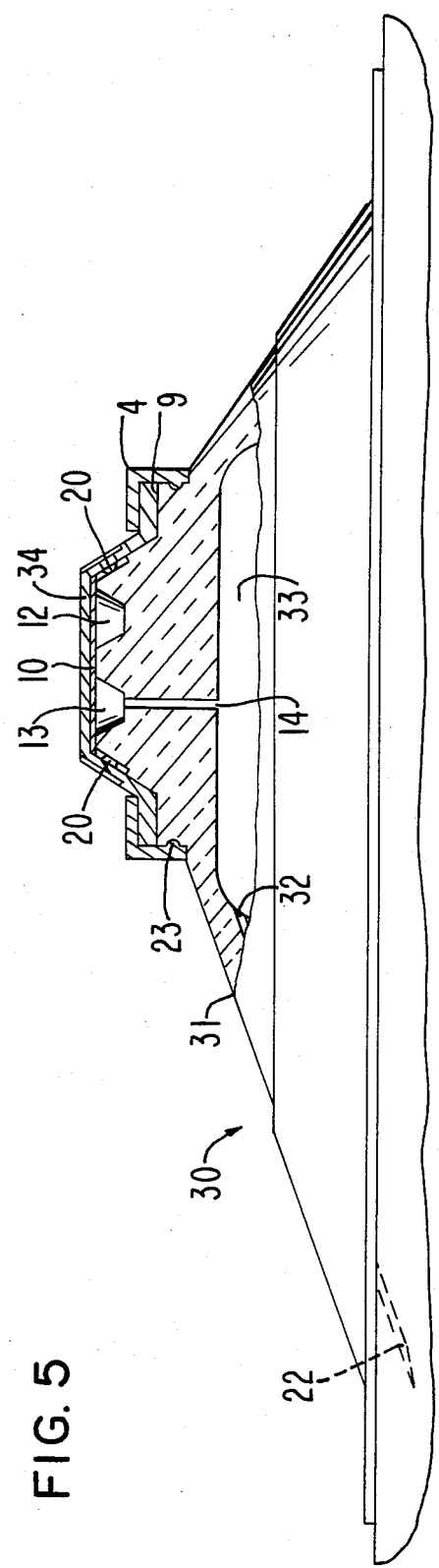

Referring now to FIGS. 4 and 5, the rotary syringe of this invention is formed as an integral part of a pump designed to produce a relatively constant basal flow rate which flow rate can be supplemented by operation of the rotary syringe of this invention. In FIGS. 4 and 5, like reference numerals in FIGS. 1–3 refer to like elements and base 3 of the rotary syringe is formed as an integral part of the top of a pump housing such as is disclosed and claimed in the aforementioned patent application, for example. Pump 30 comprises a housing 31 provided with outlet port 32 in communication with fluid chamber 33 which stores the material to be dispensed by the pump at a relatively constant rate. The upper portion of housing 31 is provided with an annular shoulder 9, a circumferential snap ring groove 23 and a semicircular depression forming reservoir 13 having outlet port 14 extending from one end thereof and into fluid communication with the upper portion of fluid chamber 33. A cap 2 provided with gasket 10 and plug 12 is maintained on shoulder 9 by means of snap ring 4. In this embodiment cap 2 is provided with port 34 located over plug 12 and inclined to direct a filling needle through the top and side of plug 12 and into communication with chamber 13, plug 12 being formed from a self-sealing elastomeric material so that it will function both as a displacement piston and as a resealable septum. The internal mechanisms of the ratchet teeth and pawls as well as the indicia shown in FIG. 1 are used for the same functions as in FIG. 1, the latter being omitted for clarity in FIG. 4. In the embodiment shown both the rotary syringe and the main drug reservoir 33 of pump 30 can be filled by introduction of the needle through port 88 which will fill not only reservoir 72, but also displacement chamber 25 through port 74. The specific structure of the pump mechanism which provides the tonic flow upon which the output from the rotary syringe of this invention may be superimposed is not shown in FIG. 5 and does not constitute a part of this invention. Many mechanical, electrical or osmotic pumps are known to the art having a drug reservoir that can be pulsed through outlet 14 in addition to those shown in the above identified patent application or U.S. Pat. No. 4,340,048, for example.

While this invention has been described with respect to certain specific embodiments thereof, it should not be construed as limited thereto. Various modifications will suggest themselves to workers skilled in the art which can be amde without departing from the scope of this invention which is limited only by the following claims wherein:

We claim:

1. A rotary syringe comprising, in combination:
   (a) a base member and a cap member rotable with respect to each other;
   (b) an arcuate recess formed in the surface of one of said members;
   (c) a plug extending from the other of said members and received in fluid sealing relationship with the surface of said arcuate recess;
   (d) an outlet extending through said base member providing fluid communication between the exterior of said base member and said arcuate recess at a point proximate one end thereof;
   (d) sealing means maintaining the abutting surfaces of said base and cap members in fluid tight relationship, and;
   (f) means for permitting rotation of said cap member with respect to said base member only in the direction which translates said plug toward said outlet; whereby upon rotation of said cap member on said base member, the plug means will be caused to traverse the arcuate recess forcing the contents of said recess through the outlet means.

2. The rotary syringe of claim 1 wherein said means permitting rotation in one direction only comprises a pawl on one of said members interacting with ratchet teeth disposed on the other of said members.

3. The rotary syringe of claim 2 wherein said first and second members are provided with cooperating indicia the relative position of which indicate the quantity of fluid remaining to be dispensed and which indicia are based on multiples of the volume discharged upon relative rotation of the first and second members equal to one ratchet tooth.

4. The rotary syringe of claim 1 wherein said sealing means comprises a gasket disposed between the abutting surfaces of said cap and base members and from which said plug member extends.

5. The rotary syringe of claim 4 further comprising inlet means extending through at least one of said base and cap members providing fluid communication between the exterior of said syringe and said arcuate recess and means for sealing said inlet means to prevent fluid from escaping therethrough.

6. The rotary syringe of claim 5 wherein said plug means is disposed in the path of said inlet means and said plug means is fabricated from a puncturable resealable material.

7. The rotary syringe of claim 1 wherein at least that portion of the cap member overlaying the arcuate recess is transparent.

* * * * *